United States Patent
Freeman et al.

(10) Patent No.: US 11,364,014 B2
(45) Date of Patent: Jun. 21, 2022

(54) ULTRASOUND SYSTEM FRONT-END CIRCUIT WITH PULSERS AND LINEAR AMPLIFIERS FOR AN ARRAY TRANSDUCER

(71) Applicant: KONINKLIJKE PHILIPS N.V., Eindhoven (NL)

(72) Inventors: Steven Russell Freeman, Seattle, WA (US); Truong Huy Nguyen, Redmond, WA (US); Manfred Bartz, Snohomish, WA (US); Jason Thanh Nguyen, Bothell, WA (US); Timothy Savord, Lowell, MA (US); Scott Owen Schweizer, Snohomish, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 306 days.

(21) Appl. No.: 16/321,201

(22) PCT Filed: Jul. 26, 2017

(86) PCT No.: PCT/EP2017/068829
§ 371 (c)(1),
(2) Date: Jan. 28, 2019

(87) PCT Pub. No.: WO2018/024556
PCT Pub. Date: Feb. 8, 2018

(65) Prior Publication Data
US 2019/0167235 A1 Jun. 6, 2019

Related U.S. Application Data

(60) Provisional application No. 62/370,797, filed on Aug. 4, 2016.

(51) Int. Cl.
*G01S 7/52* (2006.01)
*G01S 15/89* (2006.01)
*A61B 8/08* (2006.01)

(52) U.S. Cl.
CPC .......... *A61B 8/5246* (2013.01); *A61B 8/5207* (2013.01); *G01S 7/52019* (2013.01);
(Continued)

(58) Field of Classification Search
CPC . A61B 8/5246; A61B 8/5207; G01S 7/52085; G01S 7/52019; G01S 15/8915; G01S 7/52095
See application file for complete search history.

(56) References Cited

U.S. PATENT DOCUMENTS 5,269,309 A * 12/1993 Fort .................... G01H 5/00
                                                        600/447
6,106,472 A *  8/2000 Chiang ............... A61B 8/4236
                                                        600/447
(Continued)

FOREIGN PATENT DOCUMENTS

JP    2004180784 A    7/2004
JP    2008167876 A    7/2008
JP    2016115638 A    6/2016

OTHER PUBLICATIONS

Tortoli, et al., "ULA-OP: An Advanced Open Platform for Ultrasound Research", IEEE Transactions on Ultrasonics, Ferroelectrics, and Frequency Control, vol. 56, No. 10, Oct. 2009, pp. 2207-2216.
(Continued)

*Primary Examiner* — Rene T Towa

(57) ABSTRACT

Front-end circuitry for an ultrasound system is described which comprises a beamformer FPGA integrated circuit, transmit ICs with both pulse transmitters and linear waveform transmitters, transmit control and receiver ICs, and analog-to-digital converter (ADC) ICs. Waveform data for
(Continued)

both the linear and pulser transmitters is stored in the transmit control and receiver ICs, saving pins on the FPGA, which is the conventional source of this data. The ADCs couple digital echo data to the FPGA for beamforming over serial bus lines, saving additional FPGA pins over a conventional parallel data arrangement. The inclusion of both pulser and linear waveform transmit capabilities in the transmit ICs enables the use of both types of transmitters in the formation of a multi-mode image, such as use of the pulsers for Doppler beams and linear transmitters for B mode beams in the formation of a colorflow image.

15 Claims, 6 Drawing Sheets

(52) U.S. Cl.
CPC ...... *G01S 7/52085* (2013.01); *G01S 15/8915* (2013.01); *G01S 7/52095* (2013.01)

(56) References Cited

U.S. PATENT DOCUMENTS

| | | | | |
|---|---|---|---|---|
| 6,436,040 | B1* | 8/2002 | Collamore | A61B 8/02 600/437 |
| 6,469,957 | B1* | 10/2002 | Savord | G01N 29/346 367/137 |
| 6,638,228 | B1* | 10/2003 | Brock-Fisher | A61B 8/06 600/443 |
| 6,824,518 | B2* | 11/2004 | Von Behren | G01S 15/895 600/443 |
| 7,314,445 | B2 | 1/2008 | Wodnicki | |
| 2005/0228281 | A1* | 10/2005 | Nefos | A61B 8/4427 600/446 |
| 2005/0228282 | A1* | 10/2005 | Wang | A61B 8/4416 600/453 |
| 2006/0074320 | A1* | 4/2006 | Yoo | A61B 8/565 600/472 |
| 2008/0242987 | A1* | 10/2008 | Shifrin | G01S 15/895 600/443 |
| 2010/0063399 | A1* | 3/2010 | Walker | G01S 7/52079 600/459 |
| 2011/0201934 | A1 | 8/2011 | Robinson | |
| 2013/0158385 | A1* | 6/2013 | Barnes | A61B 5/055 600/411 |

OTHER PUBLICATIONS

Oguzman, et al., "Lower voltage IC technologies now enable ultrasound receiver chips with unprecedented high gain and low noise numbers", State-of-the-Art IC: Transmitter in Ultrasound Devices, Oct. 14, 2009, 10 pages.

Aydin, et al., "Design of PIC-Controlled Pulsed Ultrasonic Transmitter for Measuring Gingiva Thickness", Instrumentation Science & Technology, 2010, 38:411-420, pp. 411-420.

Ricci, et al., "Multichannel FPGA-based arbitrary waveform generator for medical ultrasound", Electronics Letters, Nov. 22, 2007, vol. 43, No. 24, 2 pages.

"Ultrasound systems can produce clearer images with TI's new TX7xx family", Electronica 2008 Briefing presentation, 13 pages (Abstract).

* cited by examiner

ULTRASOUND SYSTEM FRONT-END CIRCUIT WITH PULSERS AND LINEAR AMPLIFIERS FOR AN ARRAY TRANSDUCER

This application is the U.S. National Phase application under 35 U.S.C. § 371 of International Application No. PCT/EP2017/068829, filed on Jul. 26, 2017, which claims the benefit of Provisional Application Ser. No. 62/370,797, filed Aug. 4, 2016. These applications are hereby incorporated by reference herein.

This invention relates to medical diagnostic ultrasound systems and, in particular, to front-end circuitry with both pulsers and linear amplifiers for driving elements of a transducer array.

The front-end of an ultrasound system is that part of the system which communicates with an ultrasound probe, controlling the transmission of ultrasound from the probe transducer and receiving and initially processing the returning echo signals from the transducer. The front-end circuitry also controls related processing such as TGC amplification of the echo signals, digitization and at least some portion of the beamforming process. It is desirable that most of this circuitry be fabricated in integrated circuit (IC) form to reduce system size and weight and desirably cost. But today's ultrasound system use probes with multi-element array transducers to steer and focus beams electronically, eliminating mechanical parts in the probe. A conventional 1D (one dimensional) array size is 128 elements, although probes with 192 and 256 elements are in use, and 2D probes for 3D imaging have many thousands of transducer elements. For 2D array probes, microbeamformers are a necessity to enable use of an efficiently sized cable, although the front-end circuitry is still generally used for probe control and final beamformation.

It is also desirable for the front-end circuitry to provide a full range of capabilities, able to operate probes requiring pulse transmission and those using shaped waveform transmission, as well as those with multiline capability. It is further desirable that digitization be done prior to beamformation so that a digital beamformer can be used for all imaging applications. These requirements impose challenges for the number and layout of integrated circuit components, as they result in an increasing pin count for the integrated circuit components. These requirements would be lessened for probes with a fewer number of elements and those that use multiplexing, but multiplexing generally reduces performance and so the need to efficiently operate a 128-element array probe is minimally a desired requirement. It is an object of the present invention to provide an integrated circuit front-end for an ultrasound system which provides premium performance for a 128-element array transducer probe with IC packages having a reduced pin count for efficient configuration, packaging and p.c. board layout, and with consideration of the various types of fabrication required for ICs of different voltages and capabilities.

In accordance with the principles of the present invention, front-end circuitry for an ultrasound system is described which comprises a beamformer FPGA integrated circuit, transmit ICs with both pulse transmitters and linear waveform transmitters, transmit control and receiver ICs, and analog-to-digital converter (ADC) ICs. Only the transmit ICs require high voltages, and the transmit/receive switches are integrated in the transmit ICs, isolating the receiver ICs from high voltages. The transmitters can be trimmed to adjust the pulse slew rates, enabling the transmission of pulses with low harmonic frequency content and thus better harmonic images. Waveform data for both the linear and pulser transmitters is stored in the transmit control and receiver ICs, saving pins on the FPGA, which is the conventional source of this data. The ADCs couple digital echo data to the FPGA for beamforming over serial bus lines, saving additional FPGA pins over a conventional parallel data arrangement. The inclusion of both pulser and linear waveform transmit capabilities in the transmit ICs enables the use of both types of transmitters in the formation of a multi-mode image, such as use of the pulsers for Doppler beams and linear transmitters for B mode beams in the formation of a colorflow image.

Figure 1:
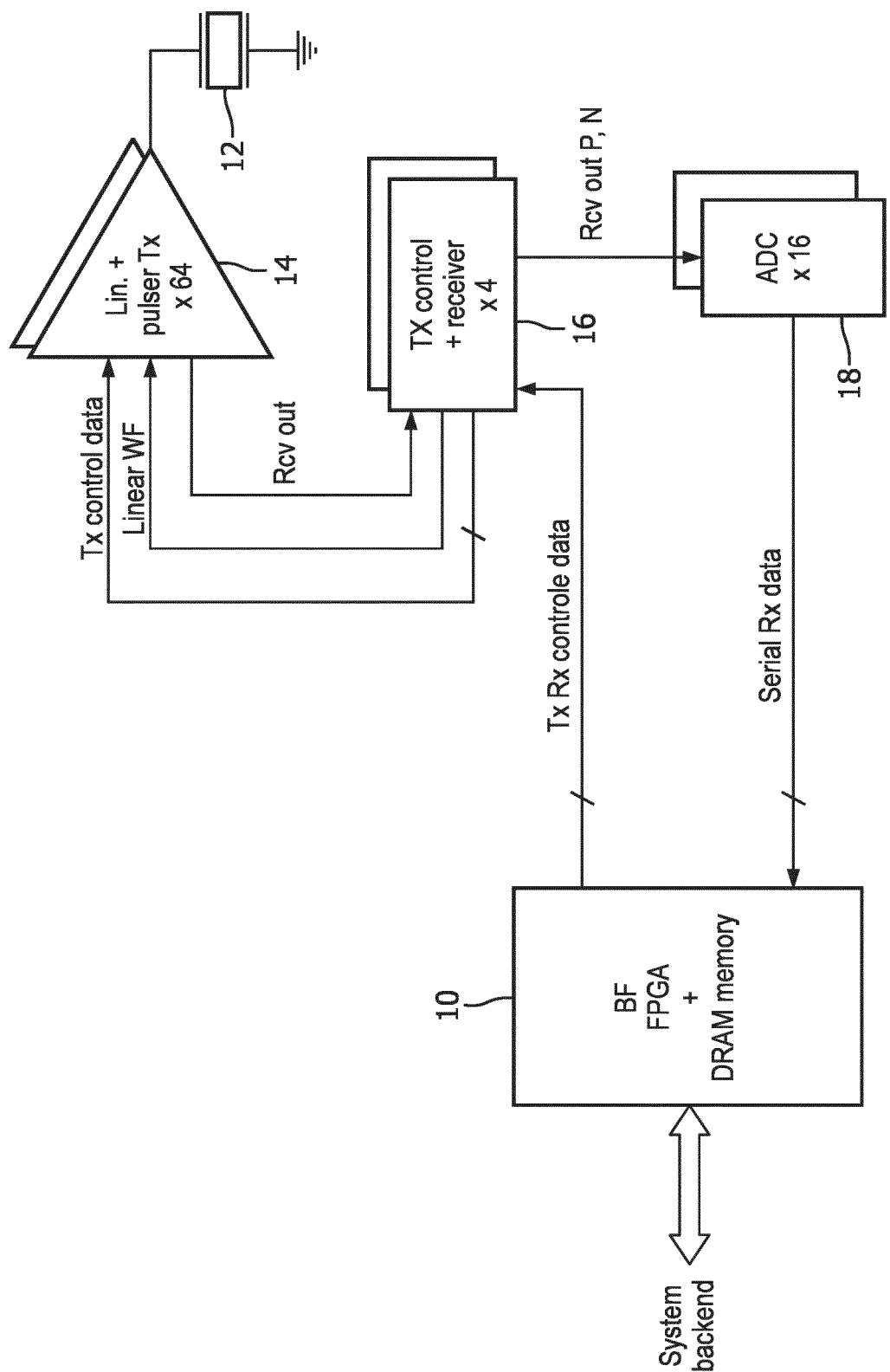
FIG. 1 illustrates in block diagram form the configuration of the ICs of an ultrasound system front-end constructed in accordance with the principles of the present invention.

Referring first to FIG. 1, the ICs of an ultrasound system front-end constructed in accordance with the principles of the present invention are shown in block diagram form. A beamformer FPGA (field programmable gate array) 10 communicates with the system backend, receiving commands for a transmit-receive imaging sequence for a probe with an array transducer and sending back digitally beamformed echo data for image formation in the backend. The FPGA 10 is configured to perform digital beamforming of received echo signals as is known in the art. Beamforming comprises receiving echo signals received by elements of a transducer array and respectively delaying the echoes to bring them into time and phase coherency, then summing them. In essence, echoes received by different elements of the array transducer from a common point in an image field are combined to produce a coherent beamformed echo signal. Analog beamformers use delay lines to delay echo signals for combining, but a digital beamformer can use a variety of delay techniques, including the relative times of sampling (digitization) of echo signals, the time to clock a sequence of digital echo signal samples through a shift register or the write-to-read time of echoes stored in a random access memory. These techniques are described in U.S. Pat. No. 4,173,007 (McKeighen et al.), for instance. Representative digital beamformers which may be implemented in FPGA 10 are shown in U.S. Pat. No. 8,137,272 (Cooley et al.) and U.S. Pat. No. 6,315,723 (Robinson et al.), for example.

The echo signals which are beamformed by the FPGA 10 are produced by ADCs 18 and stored in DRAM memory. The FPGA then extracts the data from memory as needed and beamforms the data into digital coherent echo signals, which are then communicated to the ultrasound system backend for further processing and image formation. The DRAM memory may comprise separate memory ICs which are electrically coupled to the FPGA 10. Preferably, the DRAM memory is integral to the same IC package as the FPGA. Such an integrated IC devices can be fabricated as an electronic package in which multiple integrated circuits are packaged on a unifying substrate, facilitating their use as a single component which includes the functionality and capability of multiple integrated circuit devices in a much smaller volume. Another packaging approach is to vertically stack the FPGA chip and the memory chip(s) on a p.c. board, which minimizes the packaging size (i.e., the length and width) and the footprint occupied by the chips on the circuit board. This approach, while achieving the objective of board size reduction, will not achieve one of the objects of the present invention, which is to reduce the number of pins required for the IC package, as external package pins will still be needed for the data bus, clock signal, and control lines (e.g., address lines) between the FPGA and memory ICs. A preferred implementation of the present invention is to package both the FPGA device and DRAM chips in the same IC package so that the connections between them can be made internal to the package, reducing and freeing up external pins on the FPGA package for other uses, such as connections to other ICs of the front-end.

In response to the commands for a particular transmit-receive imaging sequence, the FPGA communicates transmit and receive control data (TxRx Control Data) to transmit control and receiver ICs 16. In a preferred implementation for a 128-element transducer array, each transmit control and receiver IC 16 receives control data for operation of thirty-two elements of the transducer array. Thus, four transmit control and receiver ICs 16 are required for operation of a 128-element array. Each transmit control and receiver IC 16 responds by producing the transmit data for thirty-two elements of the array. Each IC 16 also comprises thirty-two receive signal paths including preamplifiers and TCG control for the same thirty-two elements. The transmit control and receiver ICs produce both pulse control signals and linear waveform signals for each transducer element. The transmit control and receiver ICs output a linear waveform signal for a linear transmitter and transmit control data for a pulser for each transducer element which is coupled to linear and pulser transmitter ICs 14. Also coupled to the linear and pulser transmitter ICs are control signals to control transmitter parameters such as transmitter gain and enable signals. Signal lines are also connected between the transmit control and receiver ICs 16 and the linear and pulser transmitter ICs 14 to couple received echo signals back to the TGC controlled preamplifiers of the receive signal path in the ICs 16.

In a preferred implementation each linear and pulser transmitter IC 14 comprises a pulser and linear transmitter and a transmit/receive (T/R) switch for two transducer elements 12. Thus, sixty-four linear and pulser transmitter ICs 14 are needed for a 128-element transducer array. During the receive portion of a transmit-receive cycle the T/R switches are closed to couple received signals back to the receive signal paths of the transmit control and receiver ICs. During the transmit portion of a transmit-receive cycle the T/R switches are opened to isolate the receive signal path from transmit high voltages. Thus, high voltages are needed only for the linear and pulser transmitter ICs 14, and the transmit control and receiver ICs are entirely low voltage ICs as they are completely isolated from the high voltages of transmission and have no high voltage requirement.

Echo signals received from the linear and pulser transmitter ICs 14 are amplified with TGC gain control by preamplifiers in the receive signal paths of the transmit control and receiver ICs 16 and coupled to ADC ICs 18. In a preferred implementation for a 128-element transducer array, each ADC IC 18 comprises eight ADCs for the echo signals received from eight elements of the array. Thus, each transmit control and receiver IC 16 is coupled to four ADC ICs 18. The digitized echo signals of eight transducer elements are coupled back to the FPGA 10 from each ADC IC 18 by time multiplexing over a serial receive data line (Serial Rx Data), where the digitized echo signal data is stored in the DRAM memory for use by the FPGA in beamformation. By use of serial data lines instead of parallel data lines, the number of pins required on the FPGA IC is reduced, and by time multiplexing the digitized echo signals of eight ADCs onto the same serial data line for each ADC IC, the number of pins required on the FPGA is further reduced; only sixteen serial data lines are required for the preferred implementation for a 128-element array. In the preferred implementation each serial data line is implemented as a differential pair of conductors operating in accordance with the JESD204B serial data bus format.

Figure 2:
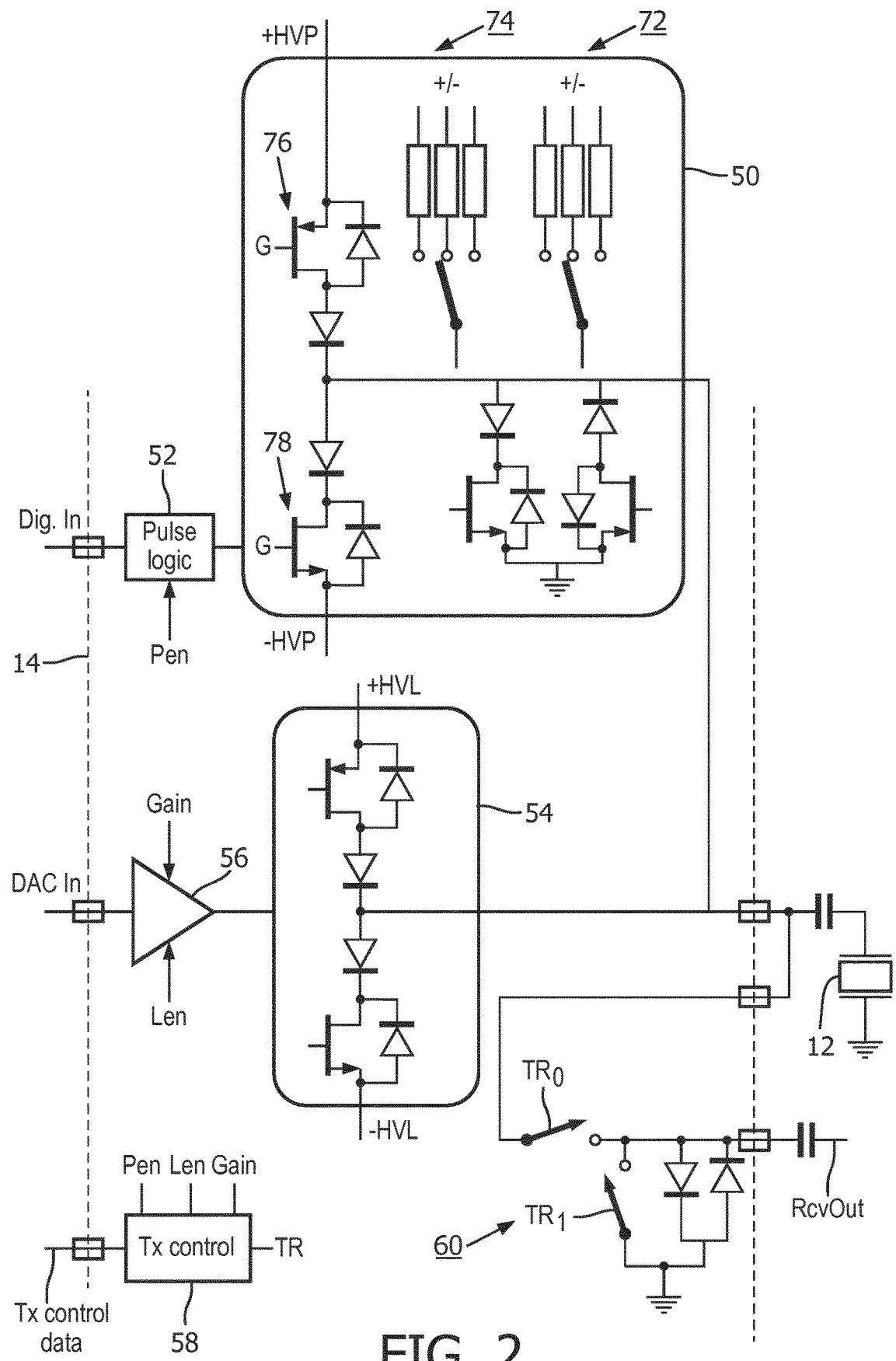
FIG. 2 is a schematic illustration of a transmit IC integrating both a pulser and a linear waveform transmitter and a transmit-receive switch on the same IC in accordance with the principles of the present invention.

FIG. 2 illustrates the circuitry of a linear and pulser transmitter IC 14 in schematic detail. Since each IC 14 in the preferred implementation operates two transducer elements 12, the circuitry of FIG. 2 is replicated twice in an IC for two transducer elements. The boundaries of the IC package are delineated by dashed lines, with the small boxes on the dashed lines indicating external connection pins of the IC package. Digital data Dig. In defines the characteristics of high voltage drive pulses produced by a pulser 50 for pulse transmission by a transducer element 12, and is applied with timing appropriate for the steering and focusing of the transmit beam to which signals from a particular element contribute. The Dig. In data is interpreted by pulse logic 52 to control the pulser 50 for production of a two-level pulse (e.g., zero and one), a three-level pulse, or a seven-level pulse. The Dig. In data comprises one bit (zero or one) for a two-level pulse, two bits for a three-level pulse, and three bits for a seven-level pulse. The pulser 50 is powered by high voltages +HVP and −HVP applied to pins of the IC 14 (not shown). An analog waveform DAC In is coupled to a pin of the IC 14 for transmission of a linear waveform such as a shaped sine wave to drive transducer element 12, again with timing appropriate for the transmit beam to which the particular element contributes. The low voltage DAC In waveform is amplified by an amplifier 56 with selectable gain and produces a waveform which is further amplified by a high power linear transmitter 54 which drives the transducer element. The linear transmitter 54 is powered by high voltages +HVL and −HVL applied to pins of the IC 14 (not shown). The outputs of both the pulser 50 and the linear transmitter 54 are coupled to the same output pin of the IC 14, to which the transducer element 12 is connected. Transmit control data (Tx Control Data) received prior to a transmission period by transmit control logic 58 determines which transmitter is to be used, the pulser 50 or the linear transmitter 54, by generation of enable signals Pen and Len for each transmitter. The pulser enable signal Pen is coupled to the pulse logic 52 and the linear transmitter enable signal Len is coupled to the amplifier 56. A gain control signal generated by the transmit control logic is also applied to the amplifier 56 for gain determination.

A T/R switch 60 is also integrated on IC 14 for each transducer element 12. The preferred T/R switch contains one single pole, single throw switch $TR_0$ in series with the receive signal path from transducer element 12 and another single pole, single throw switch $TR_1$ shunting the signal path to ground. The switches are operated in complementary fashion by the TR control signal generated by the transmit control logic 58. During transmission, when either the high voltage pulser or the linear transmitter is driving the transducer element 12, the $TR_0$ switch is open and the $TR_1$ switch is closed to isolate the receive signal path of the transmit control and receiver IC 16 from high voltages. During echo reception, when the transmitters are disabled and echo signals are received by the transducer element 12, the $TR_0$ switch is closed and the $TR_1$ switch is open to couple the received echo signals to the receive signal path by way of output line RcvOut.

The pulser 50 in a preferred implementation is commonly used for harmonic signal operation, in which harmonic frequency signals developed in the body either by tissue or contrast agents are stimulated by pulse transmission and received by the transducer array for imaging or other diagnosis. In order for the harmonic signals received by the transducer array to be as clean as possible, it is desirable that the transmitted pulses themselves contain as little high frequency content as possible, which would otherwise result in reception of signals in the harmonic frequency band which originate from the ultrasound system and not the body. To reduce harmonic frequency generation by the ultrasound system it is desirable for the transmitted pulses to be as symmetric as possible in their rise and fall times, their slew rates from one pulse level to another. Semiconductor processing, while precise for most applications, can nonetheless result in current and/or impedance differences between positive drive and negative drive MOSFETs 76, 78 of the complementary drive pulser configuration. If the positive drive transistor 76 is more conductive for a given drive signal than the negative drive transistor 78, for instance, transmit pulses will have a faster rise time (greater slew rate) at rising edges than the rate of decline at falling edges, for instance. The same effect can occur with falling edges. In accordance with a further aspect of the present invention, the drive transistors of the pulser 50 can be controllably trimmed to equalize the rise and fall characteristics of transmitted pulses. One way to do this is indicated at 72, which is to controllably change the size of a drive transistor. As indicated in the drawing, the drive transistors can be fabricated with parallel switchable channel paths between the source and drain electrodes of a MOSFET, and also for the gate electrode. As additional parallel semiconductor paths are switched in, the conductivity of the transistor is increased as the effective size of the transistor increases. When the size of the positive drive transistor 76 is increased, for instance, the rise time toward the positive voltage rail is increased, and when the size is reduced the rise time is slowed down. The sizes of the drive transistors can be controllably adjusted during manufacture or testing of the ultrasound system and test pulses applied and measured until symmetrically balanced pulses with minimal harmonic frequency content are produced. The slew rate characteristics could also be adjusted in the field, if desired. For instance, the electrical load of the transducer element seen by the pulser can also affect the rise and fall characteristics of applied drive pulses. A newly developed probe may have a transducer array which requires different trimming of the pulser transistors to achieve the best harmonic performance. When the new probe is connected to the system for a scanning procedure, data in the probe EPROM can be read by the FPGA and coupled to the linear and pulser transmitter IC 14 to reset the trimming of the pulser transistors for better harmonic performance by the new probe.

Another way to trim the pulser transistors for balanced slew rate performance is by controllable adjustment of the first stage transistors used to drive the high voltage MOSFETs. A complementary pair of power transistors such as MOSFETS 76 and 78 in FIG. 2 are generally driven by a pair of low power drive transistors coupled to their gate electrodes, which are generally operated as a balanced pair. In accordance with the present invention, such drive transistors have bias currents which can be trimmed using switchable parallel resistors 74 coupled to the transistor voltage supply as shown in FIG. 2. By adding more resistors in parallel between the supply voltage and an electrode of a drive transistor, the transistor operation is altered so that it will become more conductive, or more conductive earlier in response to a drive signal. Thus, by biasing the positive supply drive transistor for earlier or greater conductivity, the rise time of the positive power transistor 76 is increased corresponding, increasing the slew rate of a positive-going transmit pulse. By trimming the bias supplies of one or both of the drive transistors for the power transistors 76, 78 in this manner, the performance of the pulser can be adjusted to exhibit substantially identical rise times for both positive-going and negative-going pulses and pulse edges.

Figure 3:
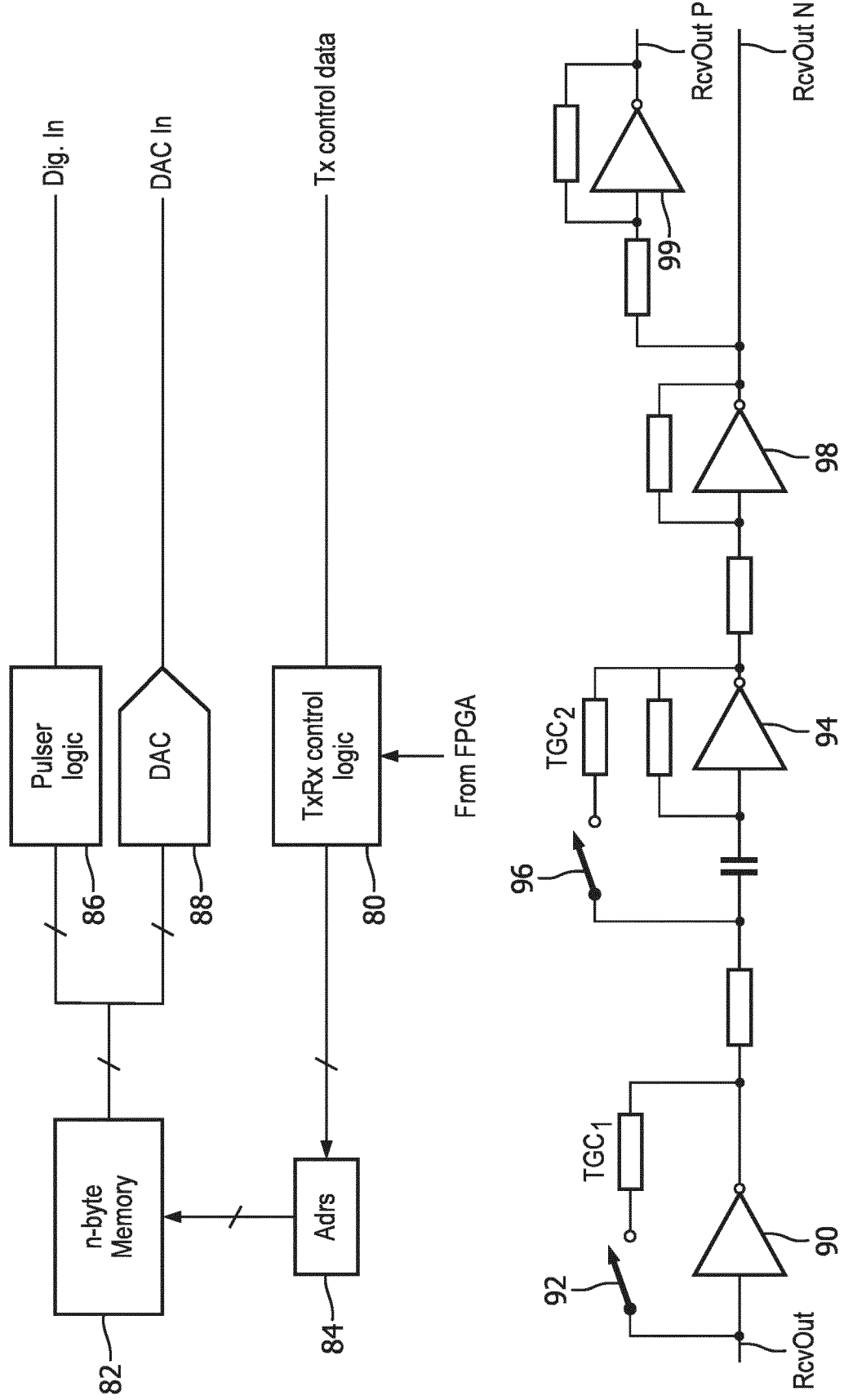
FIG. 3 is a block diagram and schematic illustration of a transmit control and receiver IC constructed in accordance with the principles of the present invention.

FIG. 3 is a block diagram and schematic drawing of the circuitry of one of the transmit control and receiver ICs 16 of FIG. 1. Each IC 16 of FIG. 1 contains the components illustrated in FIG. 3 for thirty-two transducer elements, and so the circuitry of FIG. 3 is replicated thirty-two times in each IC for a 128-element array transducer. The transmit circuitry shown at the top of the drawing comprises a transmit data memory which is an n-byte digital memory 82 containing data sequences for a plurality of different pulser pulse sequences and linear transmit waveforms. Transmit and receive control logic 80 receives control data (TxRx Control Data, FIG. 1) from the FPGA 10 which defines the transmit pulses and waveforms and the TGC control characteristic for the transmit components and receive signal path of the front-end circuitry. In response to this information an address register 84 addresses the memory locations for the n bytes of the appropriate transmit pulse or waveform stored in the memory 82. The sequence of pulse or waveform data is read out of memory 82 and applied to pulser logic 86 and to digital-to-analog converter (DAC) 88. The pulser logic 86 responds to this data by outputting a sequence of digital data bytes of the appropriate bit length for the desired pulser waveform, which is applied to the pulser input of a linear and pulser transmitter IC 14 (Dig. In). This data sequence, generally of a length of hundreds of bytes, depending on the clock frequency and desired transmit pulse resolution, causes the pulser to transmit the desired pulse shape and duration. When data for a linear waveform is read out of the memory 82, the sequence of data bytes is converted into a linearly varying analog waveform by the DAC 88, which is applied to the linear transmitter (DAC In). The transmit and receive control logic 80 also outputs control data for control of the other parameters of a transmit pulse or waveform (Tx Control Data) including the enable bits for control of pulser or linear transmitter operation and bits for control of the T/R switch 60.

The receive signal path for echo signals received by a transducer element 12 and coupled by a T/R switch 60 is shown at the bottom of FIG. 3. The echo signals (RcvOut) are applied to a first preamplifier 90 with a gain controlling $TGC_1$ resistor which is switched into circuit by a switch 92 at a time determined by the control data received by the transmit and receive control logic 80. The output of preamplifier 90 is coupled to a second gain stage 94, which includes a second switchable feedback resistor $TGC_2$ for a second stage of TGC control. The $TGC_2$ resistor is switched into circuit by a switch 96, also controlled by a signal generated by the transmit and receive control logic 80. This is followed by a third preamplifier 98. The amplified echo signals at the output of preamplifier 98 are coupled to an ADC IC 18 for digitization in the form of a complementary pair, RcvOut P produced by a further inverting preamplifier 99, and RcvOut N produced by preamplifier 98. After digitization by an ADC of one of IC chips 18, the digitized echo data is coupled to the FPGA 10 for beamformation by means of a serial data bus (Serial Rx Data). It is seen that the components and signals of the transmit control and receiver ICs 16 are all low voltage components and signals, enabling these ICs to be fabricated using an efficient low voltage CMOS process.

Figure 4:
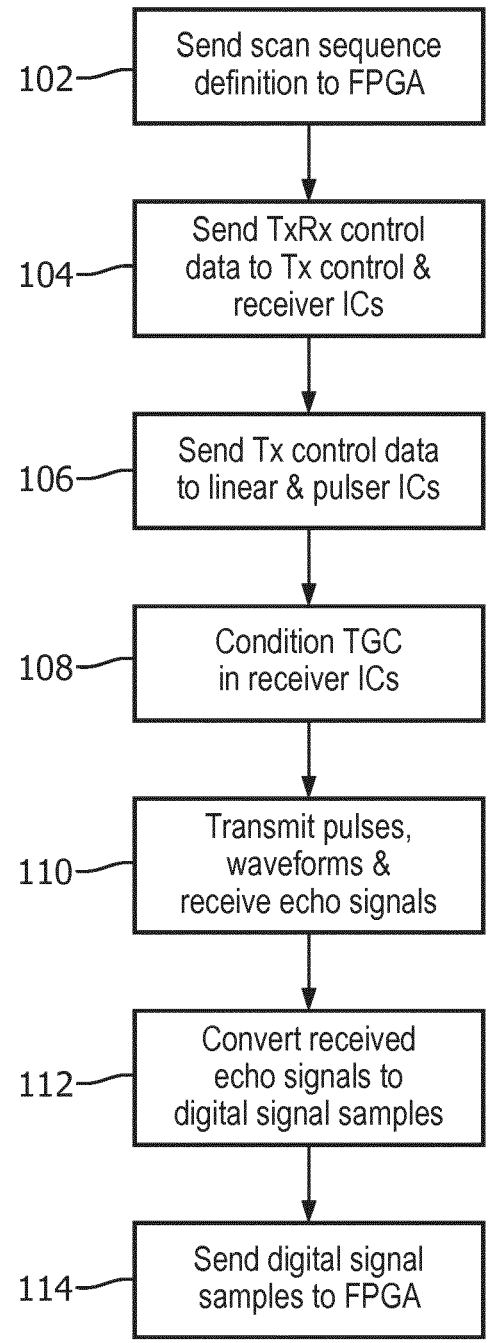
FIG. 4 is a flowchart illustrating the operation of the ultrasound system front-end circuitry of FIG. 1.

A method for operating the front-end IC circuitry of the previous drawings for an ultrasound transmit-receive scanning sequence is illustrated in FIG. 4. At the outset in step 102, information defining the scanning sequence is sent from the backend of the ultrasound system to the FPGA 10. In step 102 the FPGA 10 sends transmit and receive control data to the transmit control and receiver ICs 16. The ICs 16 in turn send transmit control data to the linear and pulser transmitter ICs 14 in step 106, and also condition the receive signal path for the desired TGC operation in step 108. The transmit waveforms are produced in the transmit control and receiver ICs 16 and applied to the enabled pulser or linear transmitter of a linear and pulser transmitter IC, causing the transmission of the desired pulse or linear waveform by the transducer elements in step 110, and the resultant reception of echo signals. The echo signals are coupled through T/R switches 60 to the receive signal paths of the transmit control and receiver ICs 16, where TGC amplification is applied. The amplified echo signals are then applied to the ADC ICs, which convert them to digital signal samples in step 112. The digital echo signal samples are then sent to the FPGA 10 in step 114 over the serial data lines for beamformation in the FPGA.

Figure 5:
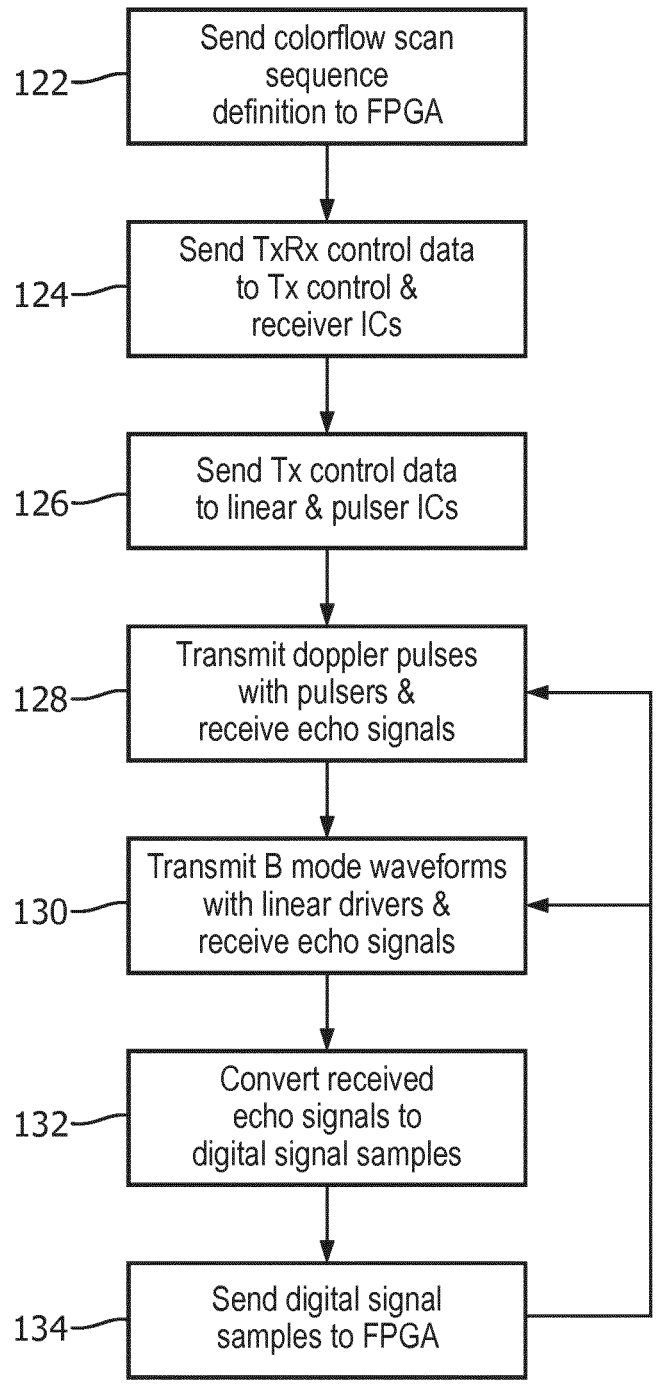
FIG. 5 is a flowchart illustrating acquisition of echo signals for a colorflow image using both the pulser and linear waveform transmitters of the ultrasound system front-end circuitry of FIGS. 1-3.

The scanning sequence of FIG. 4 can be further defined to produce a multi-mode image, such as a colorflow image, using both pulsers and linear transmitters to acquire the different modes of echo signals as shown in FIG. 5. For acquisition of echo signals for a colorflow image, operation begins with the communication of the desired colorflow scanning sequence from the backend of the ultrasound system to FPGA 10 in step 122. In step 124 control data for transmission and reception of Doppler beams for Doppler (motion) echo data and B mode beams for B mode (structural) echo data is sent to the transmit control and receiver ICs 16 (TxRx Control Data). In step 126 transmit control data for the pulsers and linear amplifiers is sent to the linear and pulser transmitter ICs 14 (Tx Control Data). The receive control data is used to control the TGC characteristic applied to received echoes in the receive signal path of the transmit control and receiver ICs. In step 128, digital data from the n-byte memories 82 is processed by the pulser logic of ICs 16 and coupled to the inputs of the pulsers 50 in the ICs 14 for transmission of a pulsed Doppler beam by the array elements 12. The echoes received in response to a Doppler beam are coupled from the transducer elements by way of the T/R switches 60 of ICs 14 to the TGC preamplifiers of the receive signal paths of ICs 16. The amplified echo signals (RcvOut P,N) are coupled to the ADC ICs 18 where they are converted to digital signal samples in step 132. The digital Doppler echo signal samples are sent (Serial Rx Data) to the FPGA DRAM memory for temporary storage in step 134 in preparation for beamforming by the FPGA into coherent echo signals received along each Doppler scanline.

For B mode scanlines a sequence of digital waveform bytes is coupled to DACs 88 from the n-byte memories, which produce linearly varying waveforms for B mode transmission. The waveforms (DAC In) are applied at appropriate times to the inputs of the amplifiers 56 for the linear transmitters 54 of ICs 14, which drive the elements of the transducer array to transmit a B mode waveform beam in step 130. In response to the B mode beam, echoes are returned from structural (e.g., tissue) matter of the subject and received by the transducer elements 12. The received B mode echo signals are coupled by way of T/R switches 60 to the receive signal paths of the ICs 16 with the same or different TGC gain characteristic as was used for the Doppler echo signals. The amplified B mode echoes are coupled to the ADC ICs 18 (RcvOut P,N) where they are converted to digital B mode echo signal samples in step 132 and forwarded to the DRAM memory of FPGA 10 (Serial Rx Data) for temporary storage and beamformation.

Since it is desired to acquire the Doppler and B mode echo signals for a given scanline at essentially the same moment in time, the transmission of Doppler pulses and B mode waveforms and resultant echo reception is generally alternated across the array. Since Doppler processing requires an ensemble of echo signals acquired over time from each point in the image field, the number of Doppler pulses exceeds the number of B mode pulses, with multiple Doppler beams being transmitted at different times along each scanline direction. The timing and degree of Doppler and B mode interleave, indicated by the arrows on the right side of FIG. 5, is determined as is known in the art in consideration of the range of tissue motion or blood flow velocities to be detected (I.e, Nyquist sampling rule,) with Doppler echoes of an ensemble being acquired over greater time intervals for measurement of lower velocities. The number of Doppler transmissions used to acquire a Doppler ensemble is dependent on considerations such as the desired accuracy of the flow and motion information.

Figure 6:
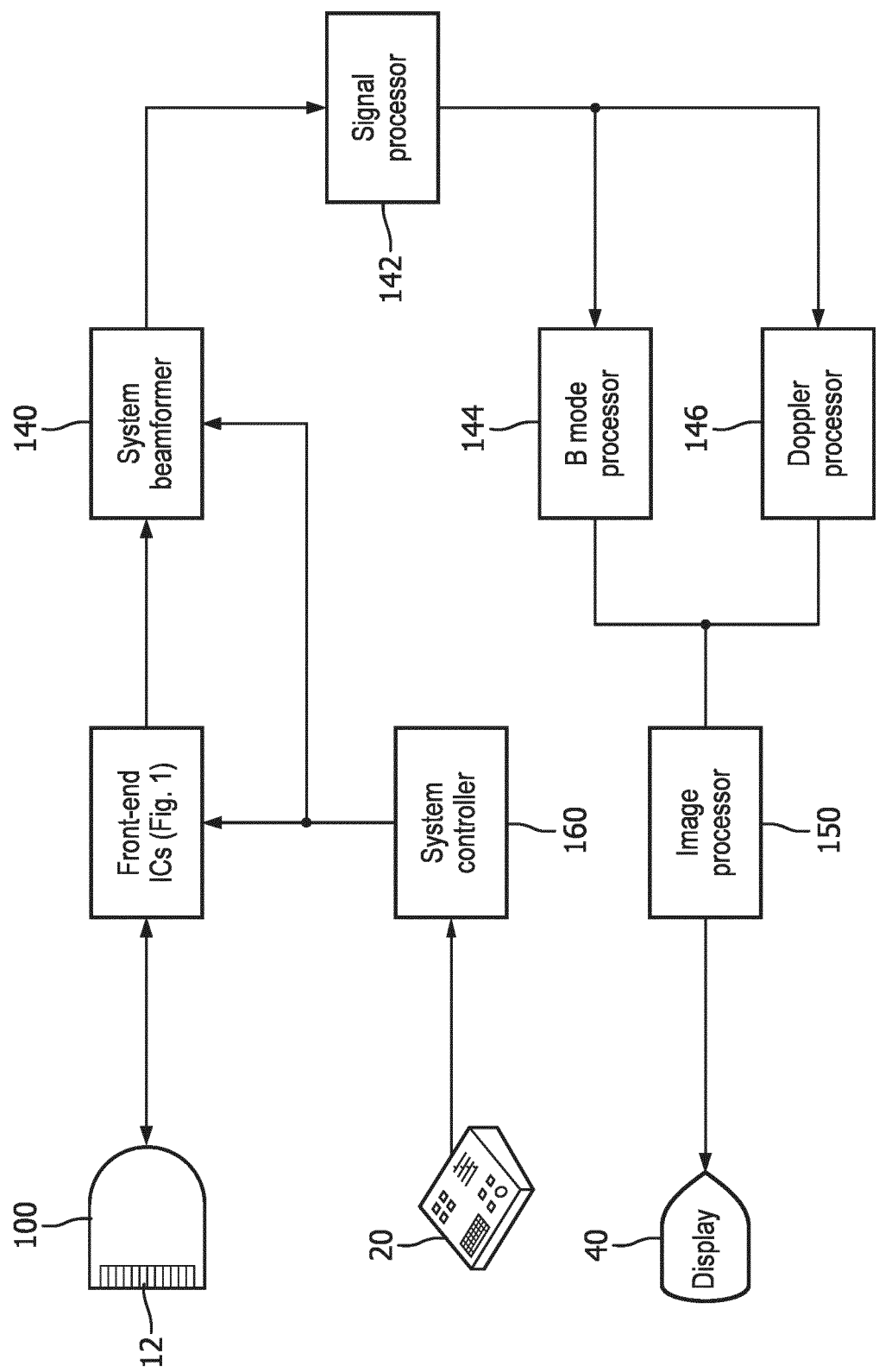
FIG. 6 illustrates in block diagram form an ultrasound system using the front-end circuitry of FIGS. 1-3.

An ultrasound system which utilizes the front-end ICs described above for the production of ultrasound images, including colorflow images, is shown in block diagram form in FIG. 6. A probe 100 having, in this example, a transducer array 12 of 128 elements is coupled to the IC front end shown in FIG. 1, in particular the transducer element pins of the linear and pulser transmitter ICs 14. The beamformer of the FPGA produces scanlines of coherent echo signals in response to pulse and waveform beams transmitted across the image field. In some implementations a second system beamformer 140 may be used to perform some of or specialized beamforming, such as the completion of beamformation from partial beamformed sums produced by the FPGA beamformer. However, in most instances the FPGA beamformer will be sufficient for all beamforming, even for those requiring complex computations such as multiline beamforming. This is particularly the case when functions commonly performed in an FPGA such as the storage of pulse and waveform characteristics and their processing is offloaded to other components, as it is in the exemplary front-end configuration of FIG. 1. In the implementation of FIG. 1 the pulse and waveform data is stored in the n-byte memories 82 of the transmit control and receiver ICs, where they not only eliminate this functionality from the FPGA but also bring it closer to the transmitter ICs where it is used. Since an FPGA can be, as its name states, field programmable, firmware can be used to reconfigure the logic elements in the FPGA into a single 128 channel beamformer for some imaging procedures, or into 2×, 4×, 8×, or even higher order multiline beamformers for the production of multiple receive beams in response to a single transmit event in other imaging procedures. Furthermore, the use of the FPGA configuration described above has demonstrated that a premium performance ultrasound system front-end with the foregoing capabilities can be realized with the use of only a single FPGA IC as illustrated in FIG. 1.

The digital coherent echo signals resulting from beamformation are processed by a signal processor 142, which performs functions such as decimation, filtering, spatial or frequency compounding and quadrature detection for Doppler processing. The processed signals are applied to a B mode processor 144, where the B mode echo signals are amplitude detected and further processed for B mode image formation. The processed signals are also applied to a Doppler processor where ensembles of Doppler echo signals are processed to estimate the Doppler shift (frequency) of flow or motion at points in the image field. For a colorflow image the Doppler frequencies are used to look up color values in a color data table so that the Doppler-measured motion can be displayed in corresponding colors. The Doppler and B mode scanlines are coupled to an image processor 150, where they are combined by scan conversion into overlays for an image of the desired display format, e.g., sector, linear or 3D. The resultant B mode, colorflow, color Doppler, or other multi-mode image is displayed on an image display 40.

User control of the ultrasound system is effected through a user control 20. Signals resulting from user interaction with the user control are coupled to a system controller 160 which coordinates the overall control of the ultrasound system, such as commanding the front-end circuitry to acquire B mode and Doppler echo signals for a desired imaging scan sequence definition, and controlling the B mode processor, the Doppler processor, and the image processor of the backend to process and combine these echo signals into a displayed colorflow or other image.

It should be noted that the various embodiments described above and illustrated by the exemplary ultrasound system of FIG. 6 may be implemented in hardware, software or a combination thereof. The various embodiments and/or components of an ultrasound system, for example, the modules, or components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system. The computer or processor may also include a memory. The memory devices described above may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasound system for multi-mode imaging, the system comprising:
   an array of transducer elements;
   a first integrated circuit comprising:
      a pulser;
      a linear transmitter; and
      a transmit/receive switch, wherein the pulser and the linear transmitter are coupled via a common output of the first integrated circuit to a common transducer element of the array, the pulser being adapted to generate transmit pulses from the common element during a first imaging mode and the linear transmitter being adapted to transmit a linear waveform from the common element during a second imaging mode;
   a different, second integrated circuit comprising:
      a beamformer coupled to the array and adapted to beamform echo signals from the array; and
      an image processor that is coupled to receive beamformed echo signals from the beamformer and adapted to produce a multi-mode image combining image data from the first imaging mode and the second imaging mode,
   wherein the pulser and the linear transmitter are adapted to be powered by a high voltage,
   wherein the transmit/receive switch is adapted to direct the high voltage away from the beamformer, and
   wherein the pulser, the linear transmitter, and the transmit/ receive switch are integrated in the first integrated circuit such that the different, second integrated circuit is isolated from the high voltage.

2. The ultrasound system of claim 1, further comprising a time gain compensation (TGC) preamplifier between the array and the beamformer.

3. The ultrasound system of claim 2, further comprising an analog-to-digital converter (ADC) between the array and the beamformer.

4. The ultrasound system of claim 1, wherein the first imaging mode comprises a colorflow imaging, and the second imaging mode comprises B-mode imaging.

5. The ultrasound system of claim 4, wherein the system is adapted to operate the pulser and the linear transmitter in a time-interleaved manner.

6. The ultrasound system of claim 5, wherein the pulser is further adapted to generate a plurality of ensembles of Doppler echo signals from points in an image field.

7. The ultrasound system of claim 4, further comprising:
 a Doppler processor having an input coupled to the beamformer and an output coupled to the image processor, the Doppler processor being adapted to process Doppler echo signals generated from the pulser; and
 a B mode processor having an input coupled to the beamformer and an output coupled to the image processor, the B mode processor being adapted to process B mode echo signals generated from the linear waveform.

8. The ultrasound system of claim 1, wherein the beamformer comprises a field-programmable gate array (FPGA) beamformer.

9. The ultrasound system of claim 1, further comprising a transmit data memory coupled to the pulser and the linear transmitter;
 wherein the transmit data memory contains transmit data bytes for both the pulser and the linear transmitter.

10. The ultrasound system of claim 9, further comprising a DAC coupled between the transmit data memory and an input of the linear transmitter.

11. The ultrasound system of claim 1, further comprising:
 a transmit data memory, coupled to inputs of the linear and pulser transmitter integrated circuit and containing transmit data bytes for both the pulser and the linear transmitter;
 a plurality of receive signal paths, each coupled to a separate transducer element of the array; and
 a plurality of integrated circuit analog-to-digital converters (ADCs), each having an input coupled to the plurality of receive signal paths and an output coupled to a serial data output line; and
 a beamformer field-programmable gate array (FPGA) integrated circuit in an integrated circuit package coupled to receive echo signals from one or more serial data output lines of the plurality of integrated circuit ADCs.

12. The ultrasound system of claim 11, wherein the transmit data memory is located on a different integrated circuit from that of the beamformer FPGA.

13. The ultrasound system of claim 11, wherein the array comprises a 128-element transducer array; and
 wherein the first integrated circuit comprises a plurality of pulsers and linear transmitters, and wherein the plurality of pulsers and linear transmitters comprises 128 pulsers each coupled to a transducer element of the array and 128 linear transmitters each coupled to a transducer element of the array.

14. The ultrasound system of claim 13, wherein the beamformer FPGA integrated circuit is adapted to receive control data for an image scanning sequence and to supply control data for the image scanning sequence to the transmit data memory and the receive signal paths;
 wherein the beamformer FPGA integrated circuit comprises a single FPGA integrated circuit.

15. The ultrasound system of claim 14, wherein the transmit data memory and a receive signal path are located on one integrated circuit.

* * * * *